United States Patent [19]

Katz et al.

[11] Patent Number: 4,548,827
[45] Date of Patent: Oct. 22, 1985

[54] SEPARATE RECOVERY OF CAFFEINE AND COFFEE SOLIDS ADSORBED ON ACTIVATED CARBON

[75] Inventors: Saul N. Katz, Monsey; George E. Proscia, West Sayville, both of N.Y.; George L. Clisura, Weehawken, N.J.

[73] Assignee: General Foods Corporation, White Plains, N.Y.

[21] Appl. No.: 363,714

[22] Filed: Mar. 30, 1982

[51] Int. Cl.⁴ .............................................. A23F 5/22
[52] U.S. Cl. .................................. 426/427; 426/422; 544/274
[58] Field of Search ............... 544/274, 275; 426/422, 426/423, 427

[56] References Cited

U.S. PATENT DOCUMENTS 2,508,545  5/1950  Shuman ............................ 544/274
4,160,042  7/1979  Farr et al. ..................... 544/274 X
4,298,736  11/1981  Katz et al. ........................ 544/274

FOREIGN PATENT DOCUMENTS 78586  12/1970  German Democratic Rep. .................................. 544/275

Primary Examiner—Joseph Golian
Attorney, Agent, or Firm—Basam E. Nabulsi; Thomas A. Marcoux; Daniel J. Donovan

[57] ABSTRACT

The present invention relates to a method of separately recovering caffeine and non-caffeine solids adsorbed on activated carbon. Activated carbon containing the adsorbed solids is contacted with an aqueous basic solution to elute the non-caffeine coffee solids. The two components are separated. The activated carbon is subsequently contacted with a concentrated aqueous acidic solution to elute the relatively pure caffeine. The two components are separated. The non-caffeine solids in the basic solution may be re-adsorbed onto the activated carbon. Essentially pure caffeine may be refined from the aqueous acidic solution.

10 Claims, No Drawings

SEPARATE RECOVERY OF CAFFEINE AND COFFEE SOLIDS ADSORBED ON ACTIVATED CARBON

TECHNICAL FIELD

This invention is directed to separately recovering caffeine and non-caffeine solids adsorbed on activated carbon. Specifically, the non-caffeine solids are eluted from the activated carbon by contacting said carbon with an aqueous basic solution. Caffeine is subsequently eluted from the activated carbon in relatively pure form by contacting said carbon with a concentrated aqueous acidic solution.

The non-caffeine solids in the basic solution may be re-adsorbed onto the activated carbon subsequent to the caffeine solution. The aqueous acidic solution is refined whereby essentially pure crystalline caffeine is obtained.

BACKGROUND ART

Much activity has been directed towards finding a suitable adsorbent for removing caffeine from an aqueous coffee extract. Activated carbon has long been known as a caffeine adsorbent but use of such carbon has been limited by the concurrent adsorption of non-caffeine coffee solids during decaffeination, making the process uneconomical. Several processes are directed to overcoming the problem as recently disclosed in commonly assigned U.S. Pat. App. Ser. Nos. 076,717 abandoned and 279,498 abandoned both to Pfluger et al. as well as in European Pat. App. No. 79102 822.8/Document No. 0,008,398. Both Pfluger et al. applications describe treating the activated carbon with a solution of one or more carbohydrates prior to decaffeinating an aqueous coffee extract.

Decaffeination with activated carbon, even by the methods disclosed above, is still hampered by the tenacity with which the caffeine adsorbs to the activated carbon, which tenacity makes regeneration of said carbon extremely difficult. Two recent disclosures, U.S. Pat. No. 4,298,736 to Katz et al. and commonly assigned U.S. Pat. App. Ser. No. 306,276 abandoned to Katz et al., describe effective techniques for removing adsorbed caffeine from activated carbon. The inventions call for contacting activated carbon containing both caffeine and non-caffeine solids with an organic acid or aqueous solution of an organic acid or an alcohol. The effect of the contact is to strip the activated carbon of substantially all material contained thereon. Though the caffeine is indeed removed, the resulting solution is low in caffeine purity; roughly 25% by weight of the total solids in solution is caffeine. The low purity renders the mixture difficult to refine. Additionally, the non-caffeine solids are rendered somewhat unusable by the refining process and can not generally be re-adsorbed onto the activated carbon bed.

It is an object of the present invention to separately recover the caffeine and non-caffeine solids adsorbed on activated carbon. A further object is to recover the caffeine in relatively pure form. Another object of the present invention is to recover the non-caffeine solids in a form suitable for re-adsorption onto the activated carbon.

DISCLOSURE OF THE INVENTION

The present invention permits the separate recovery of caffeine and non-caffeine solids adsorbed on activated carbon by the initial contact of the carbon with an aqueous basic solution followed by contact of the activated carbon with an aqueous acidic solution. The non-caffeine solids in the basic solution may, with minor treatment, be re-adsorbed onto the activated carbon.

Re-adsorption of the non-caffeine solids is advantageous in lowering the cost of decaffeinating an aqueous extract with a treated adsorbent. For instance, the Pfluger et al. patent applications describe a process of coating fresh activated carbon with a carbohydrate solution in order to reduce non-caffeine coffee solids losses during decaffenination. The present invention eliminates the use of the carbohydrate solution by providing for the re-adsorption of the non-caffeine solids. The invention is not limited to a process such as disclosed by Pfluger et al. Decaffeination of an aqueous coffee extract by an untreated activated carbon leads to the adsorption of a large amount of non-caffeine solids. These solids may also be recovered by the present invention and re-adsorbed onto the activated carbon to prevent subsequent non-caffeine solids losses.

The activated carbon contemplated for use in this invention is the spent carbon as may be obtained by operation of decaffeination processes similar to those set forth above. Said activated carbon thusly contains adsorbed caffeine, non-caffeine coffee solids and may contain carbohydrates (the carbohydrates and non-caffeine coffee solids are hereinafter together referred to as non-caffeine solids). A limited amount of non-caffeine coffee solids are adsorbed onto the activated carbon in an exchange with adsorbed carbohydrates during the decaffeination operation of the Pfluger et al. applications. As a result of the carbohydrate treatment and the limited exchange of non-caffeine coffee solids, the activated carbon contains valuable non-caffeine solids which solids are very desirable for recovery and re-adsorption onto the activated carbon.

It has been found that said non-caffeine solids may be recovered from the activated carbon separately from adsorbed caffeine by contacting the carbon with an aqueous basic solution which solution is confined to a specific range of pH. The critical range for the pH of the basic solution is between pH 8 and pH 13. A solution having less than pH 8 is not particularly effective for non-caffeine solids removal. The use of a basic solution with a pH greater than 13 will cause non-caffeine solids elution, but the caffeine remaining on the carbon tends to be destroyed by reactions well known in the art.

Provided the proper pH is maintained, a wide variety of basic solutions may be used in the present invention. For instance, aqueous solutions of potassium carbonate, potassium hydroxide or ammonium hydroxide have been discovered to work well. The concentration of any of the respective aqueous basic solutions is adjusted such that the solution is of a pH within the prescribed range. Ammonium hydroxide is convenient because any residue is easily steam stripped from the activated carbon subsequent to the contact of the basic solution and said carbon. So too, ammonium hydroxide is easily recovered from the aqueous basic solution which contains the non-caffeine solids by steam stripping prior to re-adsorption of said solids onto the activated carbon. Potassium-containing bases are preferred though because potassium is a natural constituent of coffee. Specifically, potassium hydroxide is the preferable base owing to its strength which minimizes the amount and hence, cost of the preparation of the aqueous basic solution.

Contact of the activated carbon and the aqueous basic solution is carried out in any manner providing solid-liquid contact, such as circulation of the basic solution through a bed of spent activated carbon contained in an elongated column. As noted, the pH of the aqueous solution is the critical parameter, but the temperature of the contact between said carbon and basic solution is significant as well. It has been found that the temperature of the contact should be at least 65° C. if the non-caffeine solids are to be properly eluted. Operation within the described conditions provides for removal of up to 65% by weight of the non-caffeine solids with concurrent desorption of approximately 5% by weight of the caffeine initially present on the activated carbon.

The bulk of the caffeine may be desorbed from the activated carbon by the process described in the hereinabove referred to Katz et al. patent and the hereinabove referred to Katz et al. patent application. The preferred process is set forth in the Katz et al. application wherein the activated carbon is contacted with a concentrated aqueous acetic acid solution comprising between 50% by weight and 80% by weight acetic acid. Preferably, the aqueous acid solution is at a concentration of 70% by weight acetic acid.

Use of an alkali metal base and acetic acid presents a difficulty in that an acetate salt tends to form when the two constituents are mingled. The salt has the effect of lowering the purity of the caffeine in the aqueous acidic solution. It is desirable, then, to introduce a flush step between the contact of the aqueous basic and acidic solutions with the activated carbon. Said flush step comprises contacting the activated carbon with an aqueous solution of approximately 5% by weight acetic acid. The dilute acid mingles with any basic solution which may remain on the carbon, forming the acetate salt which is then flushed from the activated carbon and subsequently discarded.

The contact of the activated carbon and the concentrated aqueous acidic solution occurs in any manner providing for good solid-liquid contact; slurrying said carbon in the concentrated acid solution is one example. The temperature at which said contact is carried out should be at least 85° C. Operation in the manner described herein permits recovery of up to 70% by weight of the caffeine initially present on the activated carbon, which caffeine has a purity of roughly 60% by weight in the aqueous acidic solution.

Regeneration of the activated carbon which has been contacted by both the basic solution and acidic solution is completed by two further processing steps. The carbon is first contacted with a quantity of fresh wash water to displace any non-adsorbed acid. Said activated carbon is subsequently steamed for a period of time whereby the remaining acid is volatilized. The regeneration steps are as described in the Katz et al. patent application.

The relatively pure caffeine in the aqueous acid solution may be recovered in any suitable manner such as steam distillation or simple evaporation of the acid. The preferred method is to first fully evaporate the solvent, leaving an aqueous caffeine solution. Caffeine may then be precipitated from said solution by cooling the same to form pure white needle-shaped crystals.

The aqueous basic solution which contains the non-caffeine solids may be made suitable for re-adsorbing said solids onto the activated carbon with only minor manipulation. Alternatively, the basic solution may be neutralized and the coffee solids contained therein may be returned to the aqueous coffee extract used in decaffeinating green coffee beans. In the case of re-adsorption, the basic solution must generally be concentrated to roughly 25% by weight non-caffeine solids because the basic solution as obtained above is typically of lower concentration. Then, the solution may be contacted directly with the activated carbon at the elevated pH in order to effect non-caffeine solids readsorption provided the temperature of said contact is sufficiently low. Another possibility is to neutralize the concentrated basic solution prior to contacting the activated carbon. Such a neutralization step eliminates the need for contact at a reduced temperature. Similarly, an ion exchange resin may be used to reduce the pH of the concentrated basic solution prior to contact with the carbon.

Whatever the manner of treatment of the basic solution chosen, contact with the activated carbon is again carried out in any vessel providing solid-liquid contact. The operating temperature depends on the pre-treatment of the basic solution. Re-adsorption of the non-caffeine solids substantially eliminates the use of the carbohydrate solution described in the previously referred to Pfluger et al. patent applications, representing a significant cost savings for the present invention.

The following examples are illustrative of certain embodiments of the present invention. The methods and results shown are not intended to limit the invention beyond what is claimed.

EXAMPLE 1

1. 76.8 g of activated carbon loaded with about 20% by weight non-caffeine solids and about 5% by weight caffeine was charged into an elongated glass column.

2. 1980 ml of 1.0% by weight potassium hydroxide solution (pH 12.7) was passed through the column at a rate of 4 ml/min. and a temperature of about 88° C.

3. About 1500 ml of water at a temperature of about 93° C. was passed through the column subsequent to the passage of the basic solution. 97.6% by weight of the non-caffeine solids initially loaded on the carbon was removed whereas 11.6% by weight of the caffeine initially loaded was removed from the carbon.

4. 2100 ml of 70% by weight acetic acid solution (pH 1.3) was then passed through the column at a rate of 4 ml/min. and a temperature of about 88° C.

The discharged acetic acid solution contained 70.9% by weight of the caffeine initially loaded on the carbon which caffeine was at a purity of 86.5% by weight.

EXAMPLE 2

A laboratory scale multi-column system run was made with six columns on stream at all times after the system reached equilibrium. The activated carbon used was from the same source as that used in Example 1. The conditions for the run were as follows:

| Contact with Basic Solution | |
| --- | --- |
| basic solution: | 1% by weight potassium hydroxide |
| pH: | 12.7 |
| temperature: | about 93° C. |
| flow rate: | 2.8 ml/min. |
| wt. of basic solution/wt of carbon: | 9.0 |
| cycle time: | 4 hours |

| -continued | |
|---|---|
| Intermediate Flush | |
| flush solution: | 5% by weight acetic acid |
| temperature: | about 93° C. |
| flow rate: | 4 ml/min. |
| wt. of flush solution/ wt. of carbon: | 3.0 |
| cycle time: | 1 hour |
| Contact with Acidic Solution | |
| acidic solution: | 70% by weight acetic acid |
| pH: | 1.3 |
| temperature: | about 93° C. |
| flow rate: | 3 ml/min. |
| wt. of acidic solution/ wt. of carbon: | 10.0 |
| cycle time: | 4 hours |

Approximately 75 g of activated carbon was loaded into the column each cycle. Contact of the basic solution removed better than 60% of the non-caffeine solids initially present on the activated carbon. Subsequent contact of the acidic solution removed an average of nearly 70% of the caffeine initially present on the carbon. The caffeine was at an average purity of 67% in the acetic acid solution.

We claim:

1. A process for separately recovering caffeine and non-caffeine solids adsorbed on activated carbon which comprises:
   (a) contacting the activated carbon, containing the adsorbed caffeine and non-caffeine solids, with an aqueous basic solution;
   (b) separating the activated carbon, containing essentially only caffeine, and said basic solution containing the desorbed non-caffeine solids;
   (c) further contacting the activated carbon containing essentially only caffeine, with an aqueous acidic solution;
   (d) separating the activated carbon and said acidic solution which solution contains the desorbed caffeine;
   (e) recovering the non-caffeine solids from the aqueous basic solution;
   (f) recovering the caffeine from the aqueous acidic solution.

2. The process of claim 1 wherein the aqueous basic solution has a pH of from 8 to 13, which solution comprises a base selected from potassium carbonate, potassium hydroxide and ammonium hydroxide.

3. The process of claim 2 wherein the aqueous basic solution is contacted with the activated carbon at a temperature of at least 60° C.

4. The process of claim 1 wherein the aqueous acidic solution comprises from 50% by weight to 80% by weight acetic acid which solution has a pH of from 1.3 to 1.8.

5. The process of claim 4 wherein the aqueous acetic solution is contacted with the activated carbon at a temperature of at least 85° C.

6. The process of claim 4 which further comprises contacting the activated carbon with an approximately 5% by weight aqueous solution of acetic acid prior to the contact of the activated carbon and the aqueous acidic solution.

7. The process of claim 1 which further comprises:
   (a) flushing the activated carbon with fresh water subsequent to the contact with the aqueous acid solution acid solution in step 1(d) of claim 1;
   (b) contacting the activated carbon with steam for a period of 2 or more hours whereby said activated carbon is fully regenerated.

8. The process of claim 1 wherein the caffeine is recovered from the aqueous acidic solution by:
   (a) evaporating the acid from the solution;
   (b) steam stripping the solution of residual acid so that an aqueous caffeine solution remains;
   (c) crystallizing the caffeine therefrom.

9. The process of claim 1 which further comprises re-adsorbing the non-caffeine solids in the solution of step 1(b) onto fresh activated carbon.

10. The process of claim 1 which further comprises returning the non-caffeine solids in the solution of step 1(b) to an aqueous coffee extract used in decaffeinating green coffee beans.

* * * * *